(12) United States Patent
Fuller et al.

(10) Patent No.: US 9,730,626 B2
(45) Date of Patent: Aug. 15, 2017

(54) METHOD AND SYSTEM FOR PROVIDING A SINGLE-USE SAFETY LANCET

(71) Applicant: INTRINSYK, LLC., Salem, NH (US)

(72) Inventors: Paul Robert Fuller, Salem, NH (US); James Keith Booker, Salem, NH (US); Thomas Ralph Gannon, Salem, NH (US)

(73) Assignee: INTRINSYK, LLC, Salem, NH (US)

( * ) Notice: Subject to any disclaimer, the term of this patent is extended or adjusted under 35 U.S.C. 154(b) by 198 days.

(21) Appl. No.: 14/607,729

(22) Filed: Jan. 28, 2015

(65) Prior Publication Data
US 2015/0297127 A1  Oct. 22, 2015

Related U.S. Application Data

(60) Provisional application No. 61/933,053, filed on Jan. 29, 2014.

(51) Int. Cl.
*A61B 17/32* (2006.01)
*A61B 5/151* (2006.01)
*A61B 5/15* (2006.01)

(52) U.S. Cl.
CPC ........ *A61B 5/15144* (2013.01); *A61B 5/1411* (2013.01); *A61B 5/150022* (2013.01); *A61B 5/15113* (2013.01); *A61B 5/15117* (2013.01); *A61B 5/150412* (2013.01); *A61B 5/150503* (2013.01); *A61B 5/150549* (2013.01); *A61B 5/150618* (2013.01); *A61B 5/150717* (2013.01); *A61B 5/150923* (2013.01)

(58) Field of Classification Search
CPC .......... A61B 5/15113; A61B 5/150022; A61B 5/150503; A61B 5/150618; A61B 5/150923; A61B 5/150549; A61B 5/15117; A61B 5/150412; A61B 5/15144; A61B 5/150717; A61B 5/1411
See application file for complete search history.

(56) References Cited

U.S. PATENT DOCUMENTS

D376,203 S    12/1996 Schraga
5,628,765 A    5/1997 Morita
(Continued)

OTHER PUBLICATIONS

PCT Patent Application Number: PCT/US15/13318; WIPO Publication No. WO 2015/116698; Title of Invention: Method and System for Providing a Single-Use Safety Lancet; International Search Report and Written Opinion of Jun. 25, 2015—4 pages.

*Primary Examiner* — Todd J Scherbel
*Assistant Examiner* — Son Dang
(74) *Attorney, Agent, or Firm* — Smith Tempel; Steven P. Wigmore

(57) ABSTRACT

A one-time/single use safety lancet system includes a body; a spring coupled to the body; a keeper having a deformable member; and a core for supporting a lancet and having an end coupled to the spring. The core further has a first latch for engaging the deformable member when the lancet system is in an armed state. The deformable member of the keeper is fractured after one use of the lancet system which prevents any subsequent arming of the lancet system. The keeper may be made part of the lancet body. The core may include a second latch, wherein the second latch permanently deforms or fractures the deformable member of the keeper after the single, one-time arming of the safety lancet system.

14 Claims, 9 Drawing Sheets

(56) References Cited

U.S. PATENT DOCUMENTS

| | | |
|---|---|---|
| 5,643,306 A | 7/1997 | Schraga |
| 5,707,384 A | 1/1998 | Kim |
| 6,136,013 A | 10/2000 | Marshall et al. |
| 6,168,606 B1 | 1/2001 | Levin et al. |
| 6,248,120 B1 | 6/2001 | Wyszogrodzki |
| 6,258,112 B1 | 7/2001 | Schraga |
| 6,514,270 B1 * | 2/2003 | Schraga ............. A61B 5/15142 606/181 |
| 6,764,496 B2 | 7/2004 | Schraga |
| 7,575,583 B1 * | 8/2009 | Schraga ............... A61B 5/1411 606/161 |
| 7,842,059 B2 | 11/2010 | Rutynowski |
| 8,052,707 B2 | 11/2011 | Karbowniczek et al. |
| 8,109,960 B2 | 2/2012 | Sarna et al. |
| 8,118,825 B2 | 2/2012 | Schraga |
| 8,142,465 B2 | 3/2012 | Jankowski et al. |
| 8,715,309 B2 * | 5/2014 | Schraga ........... A61B 5/150022 606/182 |
| 8,814,896 B2 * | 8/2014 | Schraga ............. A61B 5/15144 606/182 |
| 2003/0050656 A1 | 3/2003 | Schraga |
| 2005/0288699 A1 | 12/2005 | Schraga |
| 2006/0058828 A1 * | 3/2006 | Shi ................... A61B 5/150022 606/181 |
| 2009/0118753 A1 * | 5/2009 | Dicesare .......... A61B 5/150832 606/182 |
| 2009/0118754 A1 | 5/2009 | Wyszogrodzki et al. |
| 2010/0168775 A1 | 7/2010 | Karbowniczek et al. |
| 2010/0318111 A1 | 12/2010 | Sarna et al. |
| 2012/0203260 A1 | 8/2012 | Schraga |
| 2015/0313513 A1 * | 11/2015 | Marshall .............. A61B 5/1411 606/182 |

* cited by examiner

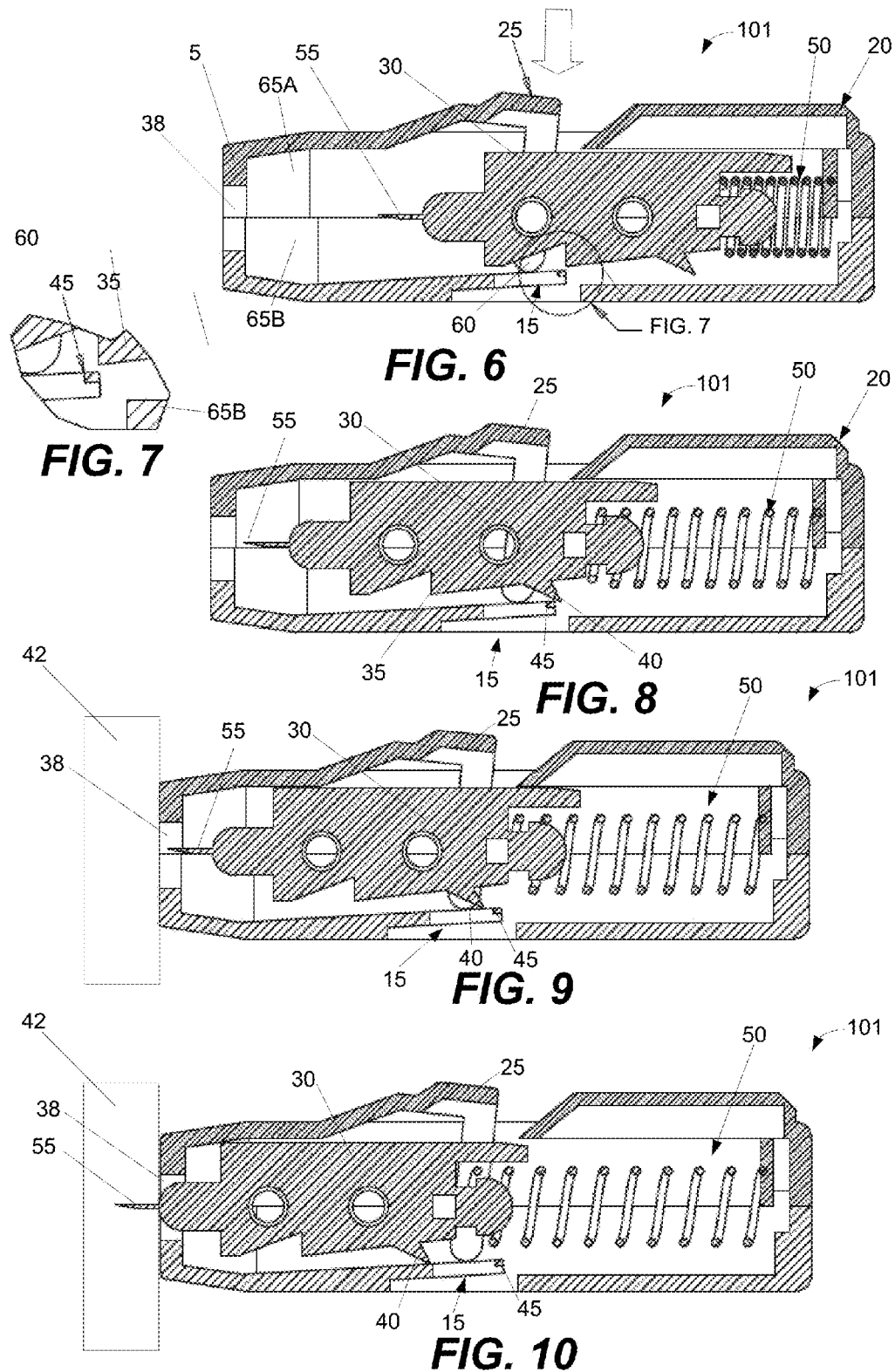

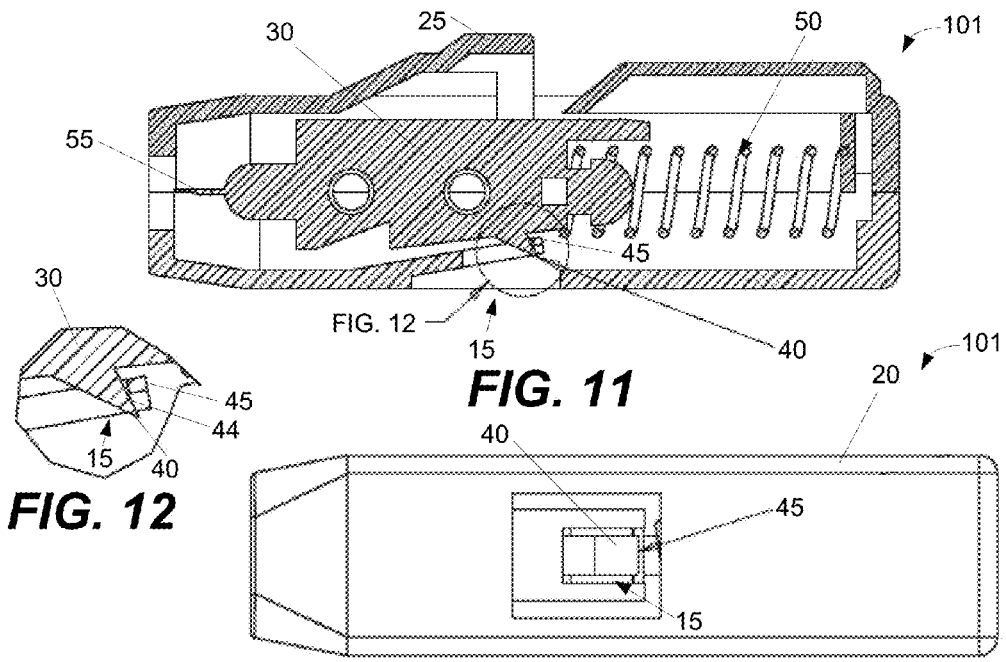
FIG. 11
FIG. 12
FIG. 13
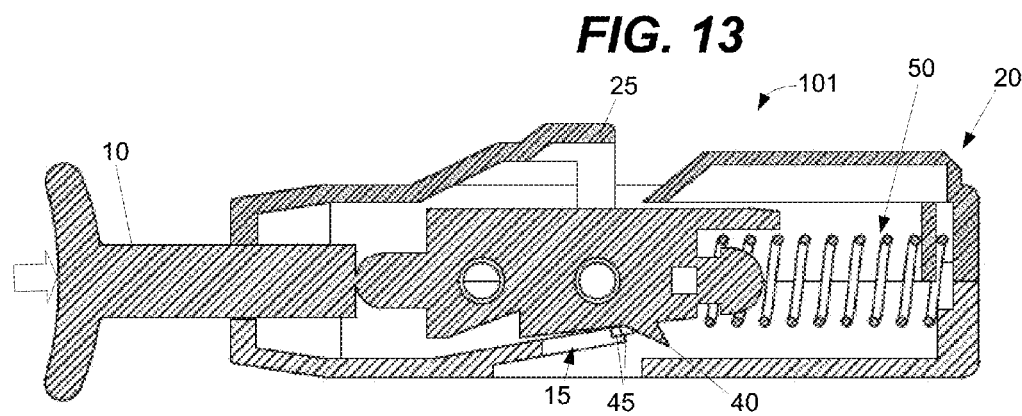
FIG. 14
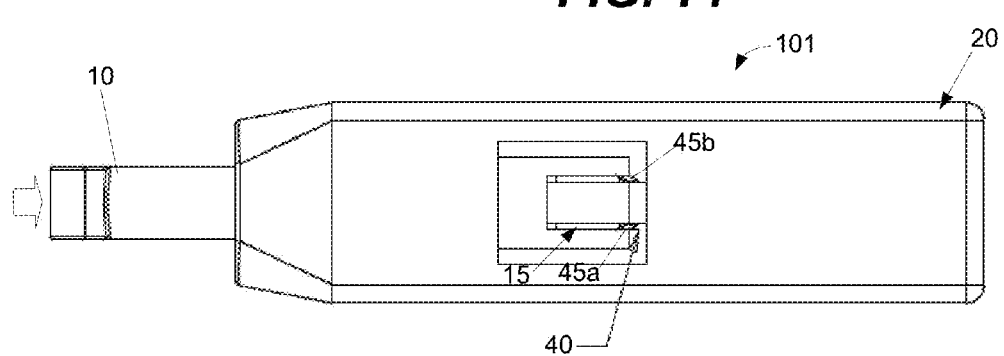
FIG. 15

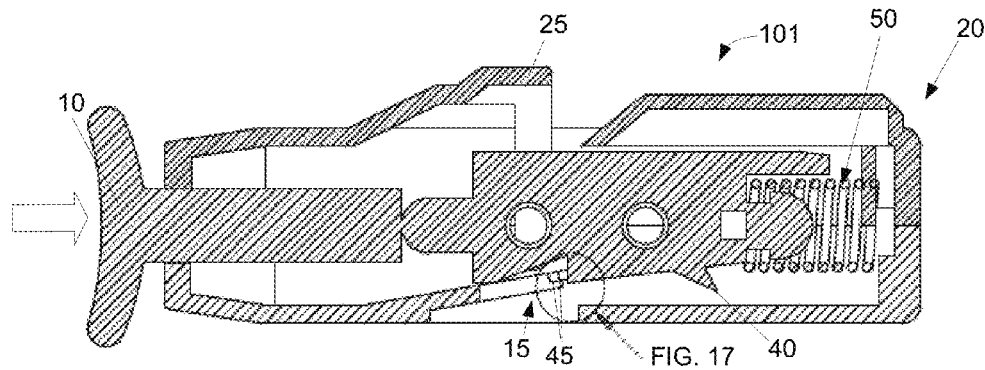
FIG. 16
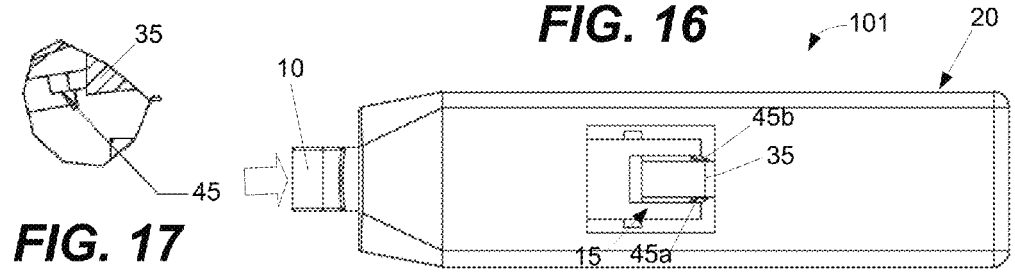
FIG. 17
FIG. 18A
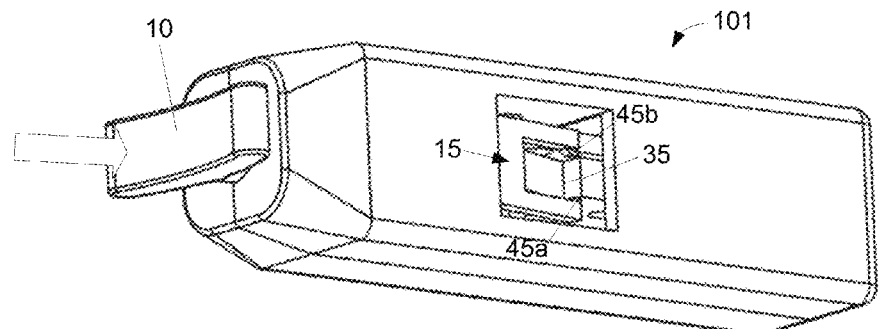
FIG. 18B
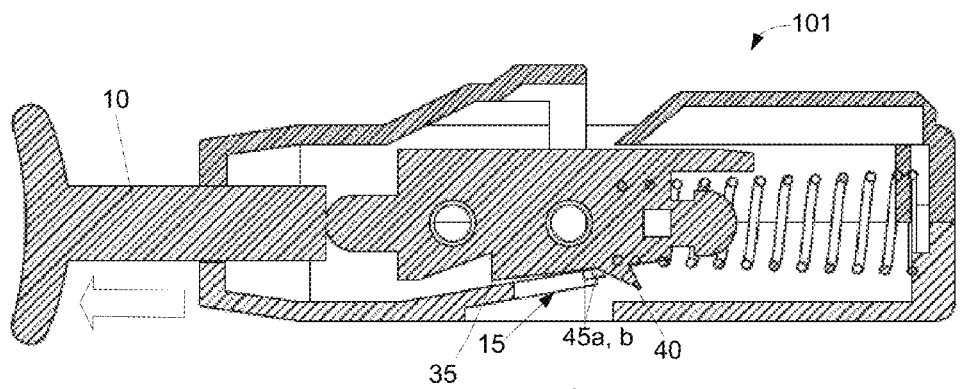
FIG. 19

METHOD AND SYSTEM FOR PROVIDING A SINGLE-USE SAFETY LANCET

BACKGROUND

Lancets are commonly utilized medical instruments which may be used in hospitals and other medical facilities. Lancets may also be used by individuals, who may have medical conditions, such as diabetes, in order to prick or pierce a patient's skin for the purpose of creating a blood sample which can be collected for testing.

Because of the wide spread use of lancets, there are a variety of lancet devices which are available in a variety of different circumstances. One type of lancet may be configured for multiple and/or repeated uses, while another category is particularly configured for single use, after which the entire device is disposed. Existing single use devices are generally effective for achieving the piercing of the skin required for effective operation.

However, such single use, disposable devices typically do not incorporate sufficient safety features to ensure the safe use and disposal of the one-time use device. Unfortunately, many conventional single use lancet devices are configured such that after a first use thereof has been achieved, it is possible for a patient to re-cock or "re-arm" the device, thereby allowing for a subsequent, inappropriate second use and subsequent uses.

Accordingly, what is needed in the art is a single use lancet system which has one or more safety features that prevent reuse of the lancet system and that may not be circumvented by an operator of the device.

SUMMARY

A one-time use lancet system includes a body; a spring coupled to the body; a keeper having a deformable member; and a core for supporting a lancet and having an end coupled to the spring. The core further has a first latch for engaging the deformable member when the lancet system is in an armed state. The deformable member is fractured after one use of the lancet system which prevents any subsequent arming of the lancet system.

The keeper may be made part of the body. The core may include a second latch, wherein the second latch permanently deforms or fractures the deformable member after arming of the lancet system.

A method for providing a single-use lancet system may include providing a body for housing a plunger, a lancet, a core, a biasing member for the core, a trigger, a first latch, a second latch, and a keeper for engaging the first and second latches. A deformable member may be included as part of the keeper and which may engage with the first and second latches. The core with the plunger may be moved into the body of the lancet system such that the deformable member engages with the first latch to place the lancet system in an armed state. After the lancet is fired, the core may move through the body towards the biasing member with the plunger such that the second latch slides along the keeper and engages the deformable member of the keeper. Upon applying a force to the plunger, the second latch of the core may permanently fracture the deformable member.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

In the drawings, like reference numerals refer to like parts throughout the various views unless otherwise indicated. For reference numerals with letter character designations such as "102A" or "102B", the letter character designations may differentiate two like parts or elements present in the same figure. Letter character designations for reference numerals may be omitted when it is intended that a reference numeral to encompass all parts having the same reference numeral in all figures.

FIG. 6 illustrates a cross-sectional view of the lancet system of FIG. 4 in which the trigger is pressed to fire the core bearing the lancet or needle towards the first end of the body according to one exemplary embodiment.

FIG. 7 illustrates an amplification of the cross-sectional view of the lancet system of FIG. 6 in which the keeper of the body no longer engages the first latch of the core according to one exemplary embodiment.

FIG. 8 illustrates a cross-sectional view of the lancet system of FIG. 1 in which the spring expands from its compressed state pushing the core such that a second latch on the core moves past the keeper on the body according to one exemplary embodiment.

FIG. 9 illustrates a cross-sectional view of the lancet system of FIG. 1 in which the spring continues to expand from its compressed state pushing the core such that the second latch on the core moves well past the keeper on the body according to one exemplary embodiment.

FIG. 10 illustrates a cross-sectional view of the lancet system of FIG. 1 in which the spring continues to expand from its compressed state pushing the core such that the lancet or needle moves outside the body of the lancet system and penetrates tissue of animal, such as a human body.

FIG. 11 illustrates a cross-sectional view of the lancet system of FIG. 10 in which the spring has contracted/retracted relative to its fully extended state in FIG. 10 such that the second latch on the core now is engaged with the keeper of the body after firing according to one exemplary embodiment.

FIG. 12 is an amplification of the a cross-sectional view of the lancet system of FIG. 11 which shows further details of how the second latch of the core engages the keeper of the body after firing of the lancet system according to one exemplary embodiment.

FIG. 13 illustrates a side view of the lancet system of FIG. 12 in which the second latch on the core now is engaged with the keeper of the body according to one exemplary embodiment.

FIG. 14 illustrates a cross-sectional view of the lancet system of FIG. 12 in which the plunger has been reintroduced and engaged with the lancet or needle and is used to push back the core such that the second latch of the core breaks the keeper on the body, such that the lancet system is now permanently disarmed according to one exemplary embodiment.

FIG. 15 illustrates a side view of the lancet system of FIG. 14 in which the plunger has pushed back the core such that the second latch of the core breaks the keeper on the body such that the lancet system is now permanently disarmed according to one exemplary embodiment.

FIG. 16 a cross-sectional view of the lancet system of FIG. 15 in which the plunger has been pushed back further relative to the view of FIG. 15 and showing how the core and its first latch have no mechanical structure on the body to engage after the keeper on the body was broken according to one exemplary embodiment.

FIG. 17 is an amplification of the cross-sectional view of the lancet system of FIG. 16 showing how the core and its first latch have no mechanical structure on the body to engage after the keeper on the body was broken according to one exemplary embodiment.

FIG. 18A is a side view of the lancet system of FIG. 16 showing how the core and its first latch have no mechanical structure on the body to engage after the keeper on the body was broken according to one exemplary embodiment.

FIG. 18B is perspective view of the lancet system of FIG. 16 also showing how the core and its first latch have no mechanical structure on the body to engage after the keeper on the body was broken according to one exemplary embodiment.

FIG. 19 is a cross-sectional view of the lancet system of FIG. 18 in which the spring has expanded from its compressed state relative to FIG. 18, but with the first latch of the core having no structure in which to engage, the lancet system remains in an unarmed state according to one exemplary embodiment.

FIG. 23B is an amplification of FIG. 23A that illustrates how the second latch on the core now has broken the keeper of the body and moved past the position of the broken keeper because the lancet has been capped and pushed back with the plunger according to one exemplary embodiment.

DETAILED DESCRIPTION

The word "exemplary" is used herein to mean "serving as an example, instance, or illustration." Any aspect described herein as "exemplary" is not necessarily to be construed as exclusive, preferred or advantageous over other aspects.

Figure 1:
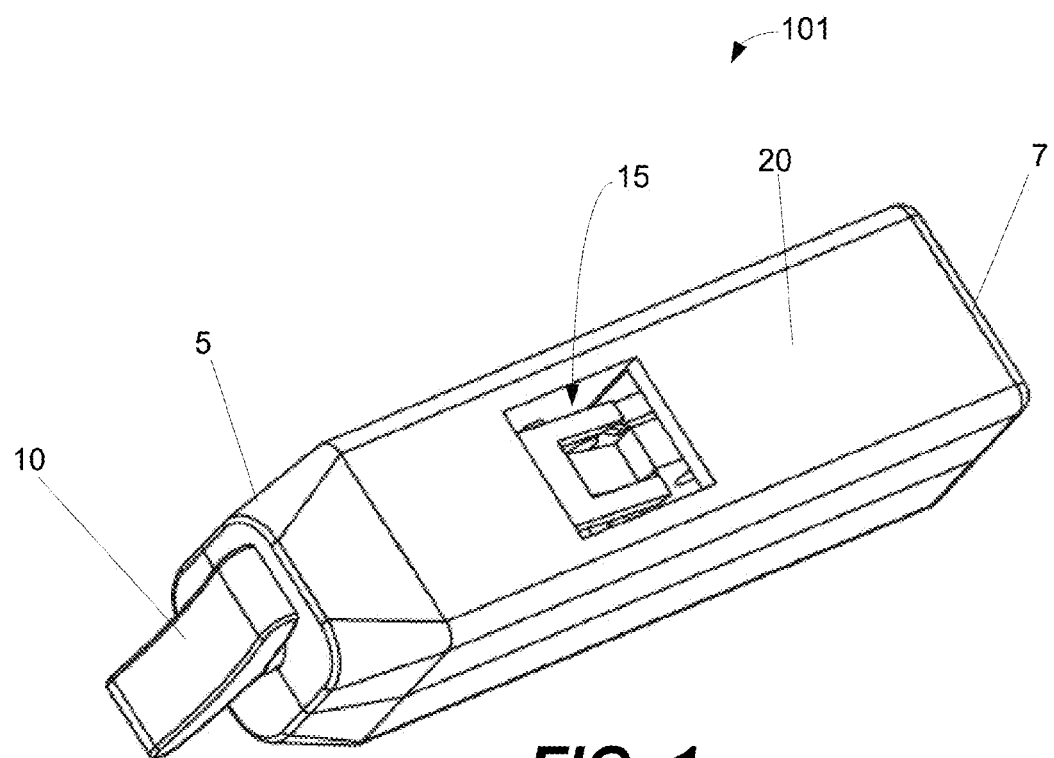
FIG. 1 illustrates a perspective view of a lancet system according to one exemplary embodiment.

Referring now to FIG. 1, this figure illustrates a perspective view of a lancet system 101 according to one exemplary embodiment. The lancet system 101 may include a plunger 10, a body 20, and a permanently deformable body keeper 15 which will be described in further detail below. The plunger 10 is moved within the body 20 in order to "arm" or "load" the lancet system 101 in which a core 30 (not illustrated in this figure but see FIG. 2) engages with the permanently deformable keeper 15. "Arming" or "Loading" the lancet system 101 means that the core 30 is ready to be launched such that it moves a lancet or needle 55 (FIG. 6) towards a patient for piercing tissue.

The plunger 10 and body 20, which includes the permanently deformable body keeper 15, may be manufactured from non-metal materials such as plastics, ceramics, and other similar lightweight materials. However, the lancet system 101 may be made from metal materials as desired and as appropriate for other types of applications as understood by one of ordinary skill in the art.

The plunger 10 usually is coupled to and surrounds and protects an actual lancet or needle 55 (see FIG. 6 described below). The lancet or needle 55 as well as a spring 50 (see FIG. 2) may be constructed from metal materials, such as, but not limited to stainless steel, rubber, plastic, and others as understood by one of ordinary skill the art.

The body 20 of the lancet system 101 may have a first end 5 and a second end 7. The first end 5 may receive the plunger 10 and it is also the end in which the lancet or needle 55 may exit to pierce tissue. The overall shape of the body 20 may comprise a rectangular parallel piped geometry. However, other shapes are possible and are within the scope of this disclosure. Other shapes include, but are not limited to, cylindrical, pentagonal, hexagonal, octagonal, etc. In the exemplary embodiment illustrated in FIG. 1, the first end 5 of the body 20 has a narrowing geometry for surrounding the aperture/opening for the lancet 55 and plunger 10. Meanwhile, the second end 7 of the body 20 has a substantially rectilinear, square-shaped geometry.

FIGS. 2-4, 6, 8-10, 12, 14, 16, 19, and 21 illustrate cross-sectional views of the lancet system 101 of FIG. 1 over the course of time—from being armed to being permanently disarmed according to one exemplary embodiment.

Figure 2:
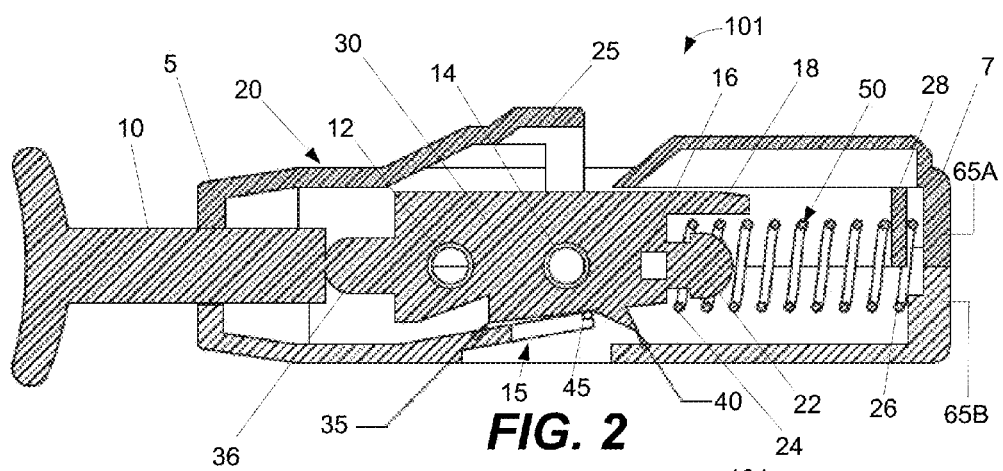
FIG. 2 illustrates cross-sectional view of the lancet system of FIG. 1 in which the lancet is in a disarmed state ready to be armed according to one exemplary embodiment.

Referring now to FIG. 2, the plunger 10 engages a movable core 30 which is biased with spring 50. The movable core 30 supports and holds in place the lancet or needle 55 (see FIG. 6) which is encased/enveloped by the plunger 10.

The movable core 30 has a first latch 35 and a second latch 40. Each of these core latches 35, 40 engage at some point in time the permanently deformable body keeper 15 of the body 20 which has the deformable member 45 during the arming of the lancet system 101. The core 30 also has several holes 12, 14, 16 as well a first end 35 and second end 22. The first and second circular shaped holes 12, 14 may be used in the manufacturing process for forming the core 30 such that these holes 12, 14 may hold the needle 55 (not visible in FIG. 2, but see FIG. 6) in place for securing to the core 30. The third square shaped hole 16 is used to stop the needle 55 within the core 30. These three holes 12, 14, and 16 are regularly used in the industry as understood by one of ordinary skill in the art.

The first end 36 of the core 30 has a dome-like shape while the second end 22 of the core has spherical shape. At the apex of the dome-like shape of the first end 36 is where the lancet or needle 55 projects (see FIG. 6) and is the end which receives and contacts the plunger 10. Meanwhile, the spherical shaped second end 22 receives at least one end 24 of the coil spring 50. The end 24 of the spring 50 may have a "snap-fit" engagement/relationship with the spherical shaped second end 22 of the core 30. The Adjacent to the second end 22 and which forms part of the core 30 is a tab 18.

Tab 18 of core 30 helps keep core 30 straight when the core 30 is launched/moved by spring 50. Tab 18 further serves to ensure that after firing of the lancet 55, it is not possible for latch 40 of core 30 to slip past post/arm 45 on keeper 15 (of the lower assembly body 20). Tab 18 does this by preventing the core 30 from tilting or rotating which in turn ensures that it is not possible for tab 40 to move past keeper 15 once post/arm 45 is permanently deformed/broken.

The first end 36 and second end 22 of core 30 may have other shapes other than those illustrated. Further, while spring 50 may comprise a coil, compression-type spring 50, other types of springs 50 may be employed without departing from the scope of this disclosure. Other types of springs 50 include, but are not limited to, tension/extension springs, torsion springs, constant springs, variable springs, helical springs, flat springs, machined springs, cantilever springs, volute springs, hairsprings, or balance springs.

In the exemplary embodiment illustrated in FIG. 2, spring 50 may have a first end 24 and a second end 26. The first end 24 of spring 50 may have a diameter of approximately 4.5 millimeters while the second end 26 of the spring 50 may have a diameter of approximately 5.7 millimeters. However, other diameters are possible and include those that range between approximately 3.0 millimeters to 12.0 millimeters for either the first end 24 or second end 26. The second end 26 of the spring 50 may be held in place/secured to the body 20 by a tab 28 that is part of the body 20 and that engages a surface of the second end 26 of the spring 50. The spring 50 may have a length of about 14.0 millimeters, a pitch of approximately 2.0 millimeters and a wire diameter of 0.50 millimeter.

However, other dimensions/sizes for the spring 50 are possible and are within the scope of this disclosure as understood by one of ordinary skill in the art. For example, a range of lengths may include one between about 6.0 millimeters to about 25.0 millimeters. A range for the pitch may include one between about 0.5 millimeter to about 5.0 millimeters. A range for the wire diameter may include one between about 0.10 millimeter to about 2.0 millimeters.

The body 20 may be formed out of at least two sections that includes a first lower half section 65B and an upper half section 65A. The lower half section 65B may have an asymmetrical shape relative to the shape of the upper half section 65A. The lower half section 65B may comprise the keeper 15 which has the deformable arm/post 45. Meanwhile, the upper half 65A may comprise the trigger button 25. While the body 20 of the illustrated embodiment is shown with two halves 65B, 65A, the body 20 may be formed in a single-body construction as appropriate and if desired by one of ordinary skill in the art. The lancet system 101 is not limited to a two-section manufactured design as understood by one of ordinary skill in the art. As noted above, most of the parts of the lancet system 101 are made from materials such as plastic. However, other materials as well as a combination of different materials are possible and are included within the scope of this disclosure such as, metal, ceramics, etc.

The trigger button 25 of the upper section 65A of body 20 is designed to contact the keeper 15 of the lower section 65B of the body 20. The trigger button 25 is used to "fire" or launch the core 30 when the core 30 is in a firing position: The firing position occurs when the plunger 10 is pushed back so that the first latch 35 of the core 30 engages the deformable arm/post 45 of the keeper 15 (See FIGS. 4-5).

Specifically, the first latch 35 on the core 30 engages the deformable keeper 15 in order to arm the lancet system 101 when it is ready to be "fired." Meanwhile, the second latch 40 on the core 30 is used to break the permanently deformable body keeper 15 (and specifically, deformable arm/post 45 of the keeper 15) if an attempt is made to re-arm the lancet system 101, which will be described in further detail below.

Figure 3:
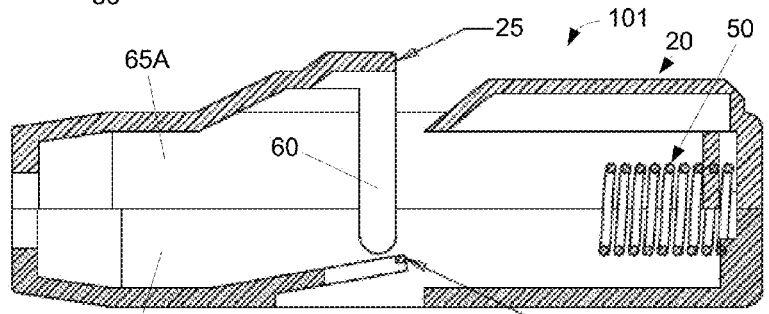
FIG. 3 illustrates cross-sectional view of the lancet system of FIG. 2 in which the core and plunger have been removed so that the entire structure of the trigger button is visible according to one exemplary embodiment.

Referring now briefly to FIG. 3, this figure illustrates a cross-sectional view of the lancet system 101 without the core 30 or plunger 10 present. The trigger button 25 has an elongated member 60 which comes in direct contact with the keeper 15 (which is part of the lower half section 65B of body 20) and which has the permanently deformable member 45. The permanently deformable member 45 may comprise a post or arm as is shown in further detail in side views of system 101 found in FIGS. 13 and 22. In this FIG. 3, the spring 50 is illustrated in a compressed state which is easily achieved when the plunger 10 (not shown in this Figure) is pressed against the core 30 (not shown in this Figure) in order to compress the spring 50.

Figure 4:
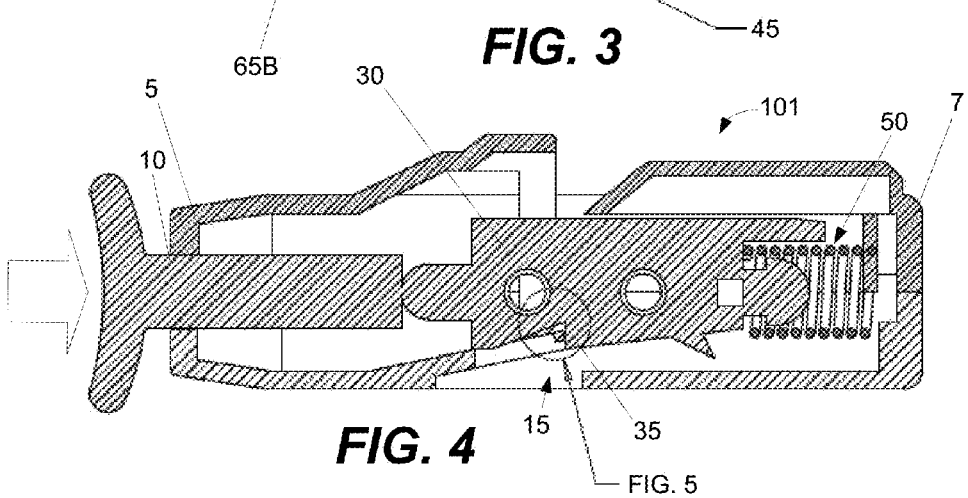
FIG. 4 illustrates a cross-sectional view of the lancet system of FIG. 1 in which the lancet has been pushed back into the body such that a first latch of the core is engaged with a keeper mechanism of the body while the spring is in a compressed state according to one exemplary embodiment.

Referring now to FIG. 4, this figure illustrates a cross-sectional view of the lancet system 101 in which the plunger 10 has been pushed inside the body 20 in order to "arm" or "load" the lancet system 101 so that it is ready to "fire": where the lancet or needle 55 may be pushed and moved by the spring 50 towards the first end 5 through an opening there through and into tissue. According to this exemplary embodiment, the core 30 has moved in a rightward direction relative to the page, towards the second end such that the spring 50 has become compressed and such that first latch 35 on the core 30 engages with the permanently, deformable member 45 of the keeper 15.

Figure 5:
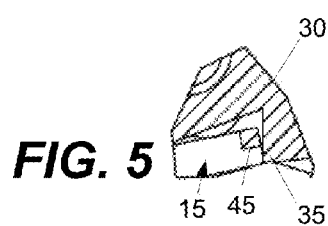
FIG. 5 illustrates an amplification of the cross-sectional view of the lancet system of FIG. 4 showing further detail of how the first latch of the core is engaged with the keeper mechanism of the body according to one exemplary embodiment.

Further details of the physical contact between the permanently, deformable member 45 and the first latch 35 on the core 30 are illustrated in FIG. 5. The deformable member 45 which is part of the keeper 15 engages the first latch 35 and holds the core 30 in a stationary position while the spring 50 is compressed and is ready to expand upon actuation of the trigger 25. As noted above, the trigger 25 is actuated/activated to "fire" the lancet system 101 when it is pressed in a downward direction relative to the page in which its elongated member 60 pushes against the keeper 15 to disengage the deformable member 45 from the first latch 35 of the core.

Referring now to FIG. 6, this figure illustrates a cross-sectional view of the lancet system 101 in which the trigger 25 has been depressed causing member 60 of trigger 25 to engage and push down on the keeper 15 of the lower section 65B of body 20. Also, as illustrated in this figure, the plunger 10 has been removed from the system 101 exposing the lancet or needle 55. With the plunger 10 removed from the lancet system 101, this removal exposes the aperture 38 in the first end 5 of the lancet system 101 through which the lancet or needle 55 will move through to engage tissue 42 (See FIG. 10).

The lancet or needle 55 may have different sizes depending upon its application. According to one exemplary embodiment, the lancet or needle 55 may comprise an industry gage of between a 15 gage and 35 gage, and more preferably, between a 20 gage and 30 gage. The length of the needle 55 may also vary depending upon its application. The needle 55 may comprise a length between about 1.2 millimeters to about 3.0 millimeters, and more preferably, between about 1.8 millimeters to about 2.2 millimeters. However, other lengths and gages are possible and are included within the scope of this disclosure.

Movement of the keeper 15 of body 20 in a downward fashion relative to the page causes the deformable member 45 of the keeper 15 to disengage with the first latch 35 of the core 30 as illustrated in further detail in FIG. 7. With the first latch 35 of the core 30 disengaged from the deformable number 45, the spring 50 is free to push/launch/fire the core 30 having the lancet 55 towards the opposite end of the body 20 through the aperture 38 for piercing tissue 42 (See FIGS. 9-10) of an organism.

Referring now to FIGS. 8-9, these figures illustrate a cross-sectional view of the lancet system 101 in which the core 30 having its second latch 40 passes or moves by the keeper 15 having the deformable member 45 that is part of the body 20. FIG. 8 illustrates how the spring 50 has expanded from its compressed state to a more uncompressed state and moving/launching the core 30 with its lancet 55 towards the patient for piercing tissue 42 (See FIGS. 9-10). Specifically, FIG. 8 illustrates the second latch 40 just moving over deformable member 45 of keeper 15. FIG. 9 illustrates further movement of the core 30 and its latch past keeper 15 and its deformable member 45 relative to FIG. 8.

Referring now FIG. 10, this figure illustrates a cross-sectional view of the lancet system 101 in which the core 30 and the lancet 55 have traveled a maximum distance permitted by the body 20 that holds the spring 50. As illustrated in this figure, the lancet 55 is now exposed and exists outside of the body 20 of the lancet system 101 and penetrates tissue 42. Meanwhile, the keeper 15 which was biased by trigger button 25 begins to elevate an upward fashion relative to the page.

Referring now to FIG. 11, this figure illustrates further detail of how the second core latch 40 engages with the deformable member 45 of the keeper 15. This engagement or contact between the second core latch 40 and the deformable member 45 occurs because the body keeper 15 is biased and raises an upward fashion relative to the page after the core 30 has passed by the body keeper 15 during a piercing operation.

Referring now to FIG. 12, this figure illustrates an amplified view of the lancet system 101 in which the keeper 15 having its deformable member 45 is fully engaged with the second core latch 40 of the core 30. This figure illustrates how the spring 50 has pulled the core 30 back within the body 20 such that the lancet 55 is no longer exposed or present/existing outside of the body 20. In this state, the deformable member 45 of the body keeper 15 is intact and is in an unfailed state.

As illustrated in FIG. 12, the cross-sectional shape of second latch 40 is substantially triangular. The triangular cross-sectional shape has at least one side 44 that contacts the deformable member 45 of keeper 15. The at least one side 44 has an angle such that the deformable member 45 "rides-up" the one side 44 as the core 30 is pushed back into the body 20 of the lancet system 101. Also, the cross-sectional shape of the deformable member 45 is substantially rectangular. However, both the deformable member 45 and the latch 40 may have shapes other than those illustrated. For example, other cross sectional shapes include, but are not limited to round, elliptical square, pentagonal, hexagonal, octagonal, etc.

FIG. 13 illustrates a side view of the lancet system of FIG. 12 in which the second latch 40 on the core 30 now is engaged with the keeper 15 of the body according to one exemplary embodiment. As illustrated in this figure, second latch 40 engages deformable member 45 of keeper 15.

FIG. 13 illustrates a "bottom" external view of the lancet system 101 (relative to the "top" external view which may have the trigger button 25, such that the body keeper 15 having its deformable member 45 engaged with the second core latch 40 are visible to an operator. As illustrated in this figure, the deformable member 45 is a relatively thin member compared to the thickness/mass of the second latch 40 of the core 30. Starting from the position illustrated in FIG. 13, if an operator of the lancet system 101 were to use the plunger 10 to attempt to rearm the lancet system 101 by using the plunger 10 to push the core 30 back into the body 20, such a force exerted by the plunger 10 would cause the second core latch 40 of the core 30 to permanently deform or break the deformable member 45 of the body keeper 15.

Referring now to FIG. 14, this figure illustrates a cross-sectional view of the lancet system 101 in which the plunger 10 has been used to push back the core 30, which in turn, causes the second core latch 40 to permanently deform or break the deformable member 45 of the body keeper 15. This figure shows the deformable member 45 in a broken state in which the deformable member 45 breaks away from its earlier position so that the second latch 40 may move past the deformable member 45.

In FIG. 15, a "bottom" external view of the lancet system 101 is illustrated and shows how the deformable member 45 has been fractured or broken in two pieces 45a, 45b by the second core latch 40 of the core 30. The deformable member 45 may deform into two pieces or it may deform by breaking off as a single piece. In other instances, the deformable member 45 may break away/off relative to the keeper 15 into more than two pieces. The extent of damage to the deformable member 45 may vary from lancet system 101 to lancet system 101 and may correspond with the amount of force applied to the plunger 10 as understood by one of ordinary skill in the art.

Referring now to FIG. 16, this figure illustrates a cross-sectional view of the lancet system 101 in which the deformable member 45 has been permanently deformed or fractured so that the first core latch 35 can no longer engage the keeper 15 of the body 20 because of the absence of the deformable member 45. According to this FIG. 16, the operator is trying to re-arm the lancet system 101 by pushing back the plunger 10 towards the spring or biasing member 50. However, the first latch 35 has no structure in which to engage or hold it in an "armed" position in order to keep the spring 50 in a compressed state. FIG. 17 shows this lack of engagement for the first core latch 35 in further detail. Similarly, FIG. 18A also illustrates a "bottom" view of the lancet system 101 (relative to the "top" of lancet system 101 which has the trigger 25) which shows how the keeper 15 can no longer engage the core 30 because of the lack of presence of the deformable member 45. FIG. 18B is perspective view of the lancet system 101 of FIG. 16 also showing how the core 30 and its first latch 35 have no mechanical structure on the body 20 to engage after the keeper 15 of the body 20 was broken (specifically, deformable member 45 of keeper 15 being fractured).

FIGS. 16 and 18 demonstrate that when the first core latch 35 of the core 30 cannot engage the keeper 15, then no mechanical energy may be stored in spring 50 to "fire" the core 30 and its lancet 55 outside of the body 20. After the deformable member 45 has been removed or permanently fractured, the core 30 may be moved back and forth with the plunger 10 as FIGS. 16-19 demonstrate, however, the lancet system 101 can no longer be rearmed in which the core 30 is held in place next to the spring 50 such that the plunger 10 can be removed before any "firing" of the core 30 having lancet 55.

Figure 20:
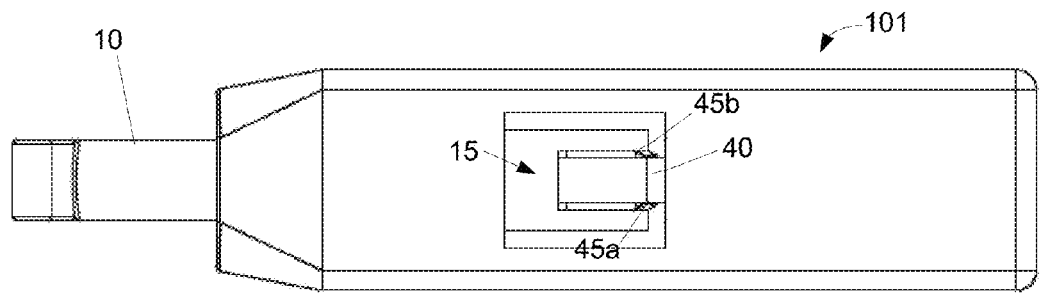
FIG. 20 is a side view of the lancet system of FIG. 19 in which the spring has expanded from its compressed state relative to FIG. 18, but with the first latch of the core having no structure in which to engage, the lancet system remains in an unarmed state according to one exemplary embodiment.

FIG. 19 illustrates a cross-sectional view of the lancet system 101 in which the core 30 and the spring 50 return to a rest state after the plunger 10 has been released by an operator who attempted to rearm the lancet system 101 as illustrated in FIGS. 16-18. If the plunger 10 is removed at this point in time, the core 30 having its lancet 55 still remains entirely contained by the body 20 such that access or physical contact to the lancet 55 is not possible. FIG. 20 illustrates a "bottom" view of the lancet system 101 which corresponds with the rest position of the core 30 illustrated in FIG. 19.

Figure 21:
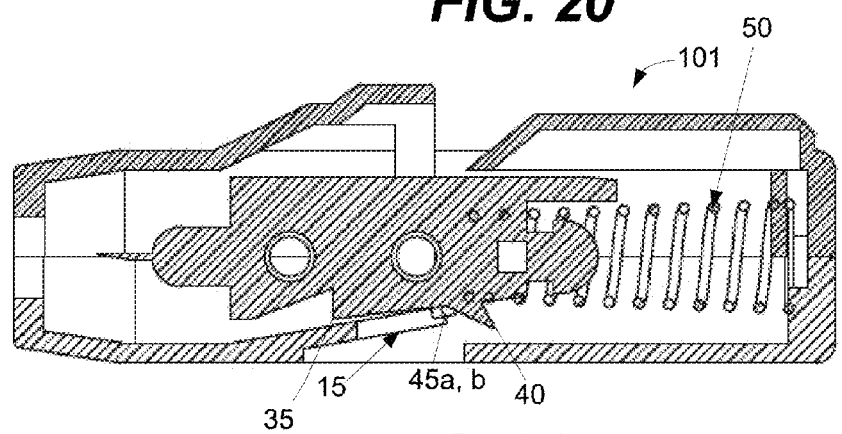
FIG. 21 is a cross-sectional view of the lancet system of FIG. 20 in which the plunger has been removed, but similar to the prior illustrations, with the first latch of the core having no structure in which to engage, the lancet system remains in an unarmed state according to one exemplary embodiment.

FIG. 21 illustrates a cross-sectional view of the lancet system 101 in which the core 30 and lancet 55 along with the spring 50 are in a rest state after the deformable member 45 of the body keeper 15 has been permanently fractured or removed. This figure also illustrates the lancet system 101 with the plunger 10 removed from the system 101.

Figure 22:
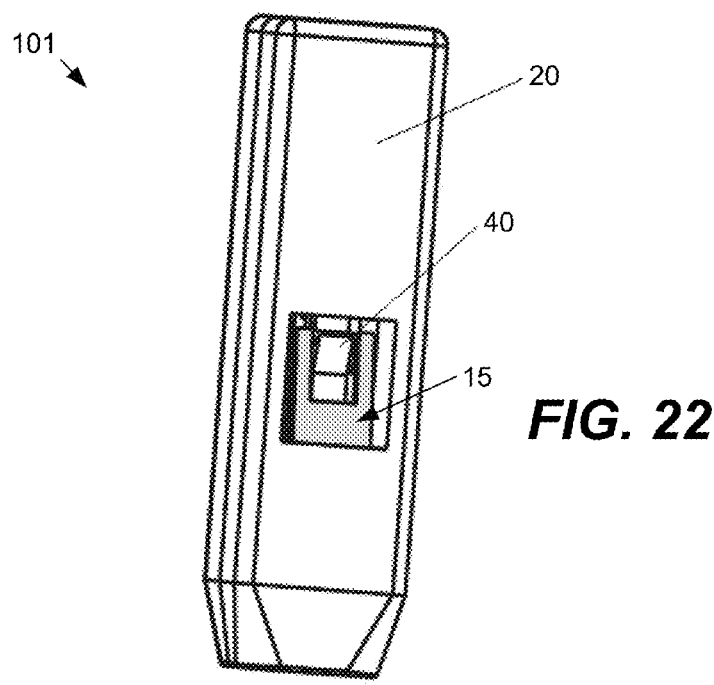
FIG. 22 is a side view of FIG. 11 that illustrates how the spring has contracted/retracted relative to its fully extended state in FIG. 11 such that the second latch on the core now is engaged with the keeper of the body after lancet has been fired according to one exemplary embodiment.

FIG. 22 illustrates a perspective "bottom" view of the lancet system 101 in which the deformable member 45 of the body keeper 15 is present (though member 45 is not visible in this figure) and is engaging the second latch 40 of the core 30. FIG. 22 illustrates the lancet system 101 in an unarmed state after "firing" of the lancet 55. The keeper 15 has shading so that the boundaries between the second core latch 40 and keeper 15 are more visible. In this exemplary embodiment, the plunger 10 has not yet been inserted to engage the core 30.

Figure 23A:
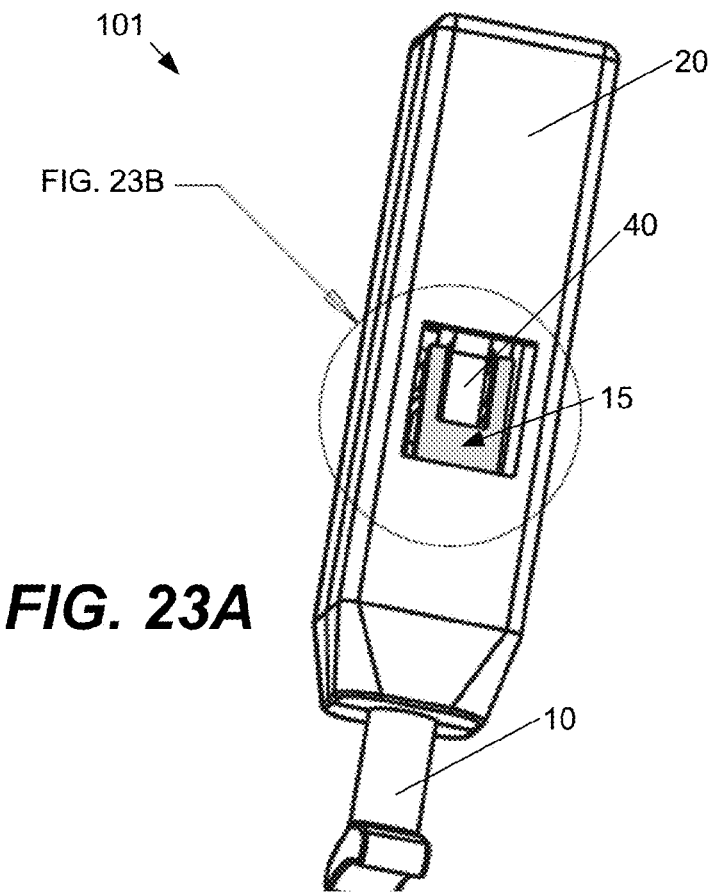
FIG. 23A is a side view of FIG. 22 that illustrates how the second latch on the core now has broken the keeper of the body and moved past the position of the broken keeper because the lancet has been capped and pushed back with the plunger according to one exemplary embodiment.
Figure 23B:
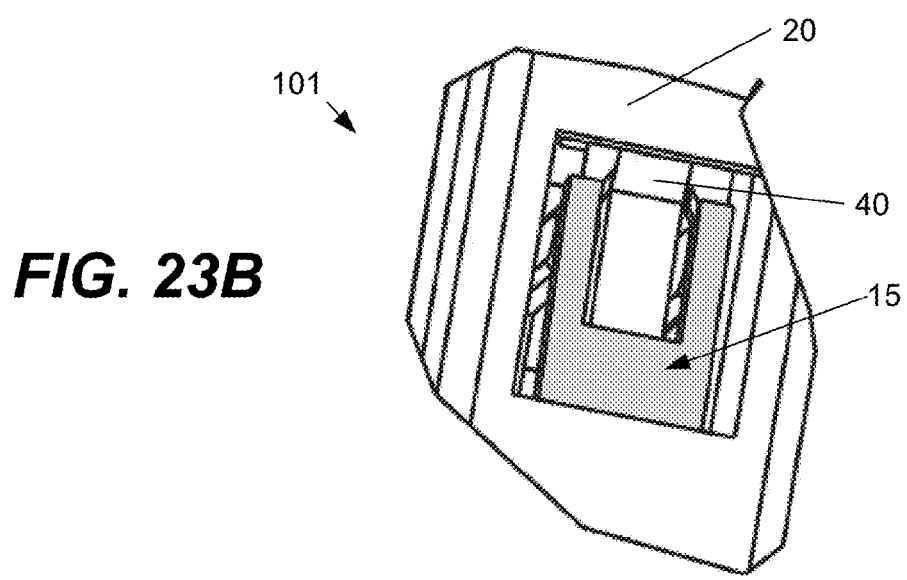
FIG. 23B is a side view of FIG. 22 that illustrates how the second latch on the core now has broken the keeper of the body and moved past the position of the broken keeper because the lancet has been capped and pushed back with the plunger according to one exemplary embodiment.

FIG. 23A illustrates a perspective "bottom" view of the lancet system 101 in which the deformable member 45 of the body keeper 15 has been deformed or fractured by the second core latch 45 of the core 30. FIG. 23A illustrates the lancet system 101 in an "unarmed" state. Keeper 15 of the body 20 has shading so that the boundaries between the core latch 40 and keeper 15 are more visible. FIG. 23B shows a magnified view of FIG. 23A in which the second core latch 45 has moved past the keeper 15 of body 20 and has fractured deformable member 45.

Figure 24:
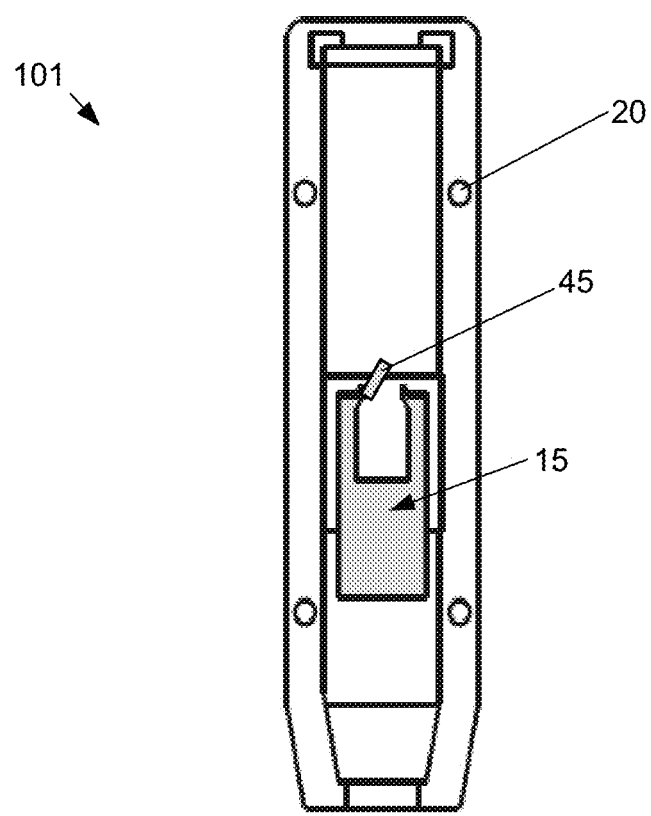
FIG. 24 is a side view of FIG. 23 that illustrates the broken keeper of the body which was permanently deformed by the second latch of the core according to one exemplary embodiment.

FIG. 24 illustrates a bottom view of the body keeper 15 and the deformable member 45 in a permanently fractured or broken state after the second core latch 40 of the core 30 has fractured the deformable member 45. Only the half of the body 20 comprising the keeper 15 and deformable member 45 are illustrated. The core 30 is not shown in this figure.

Figure 25:
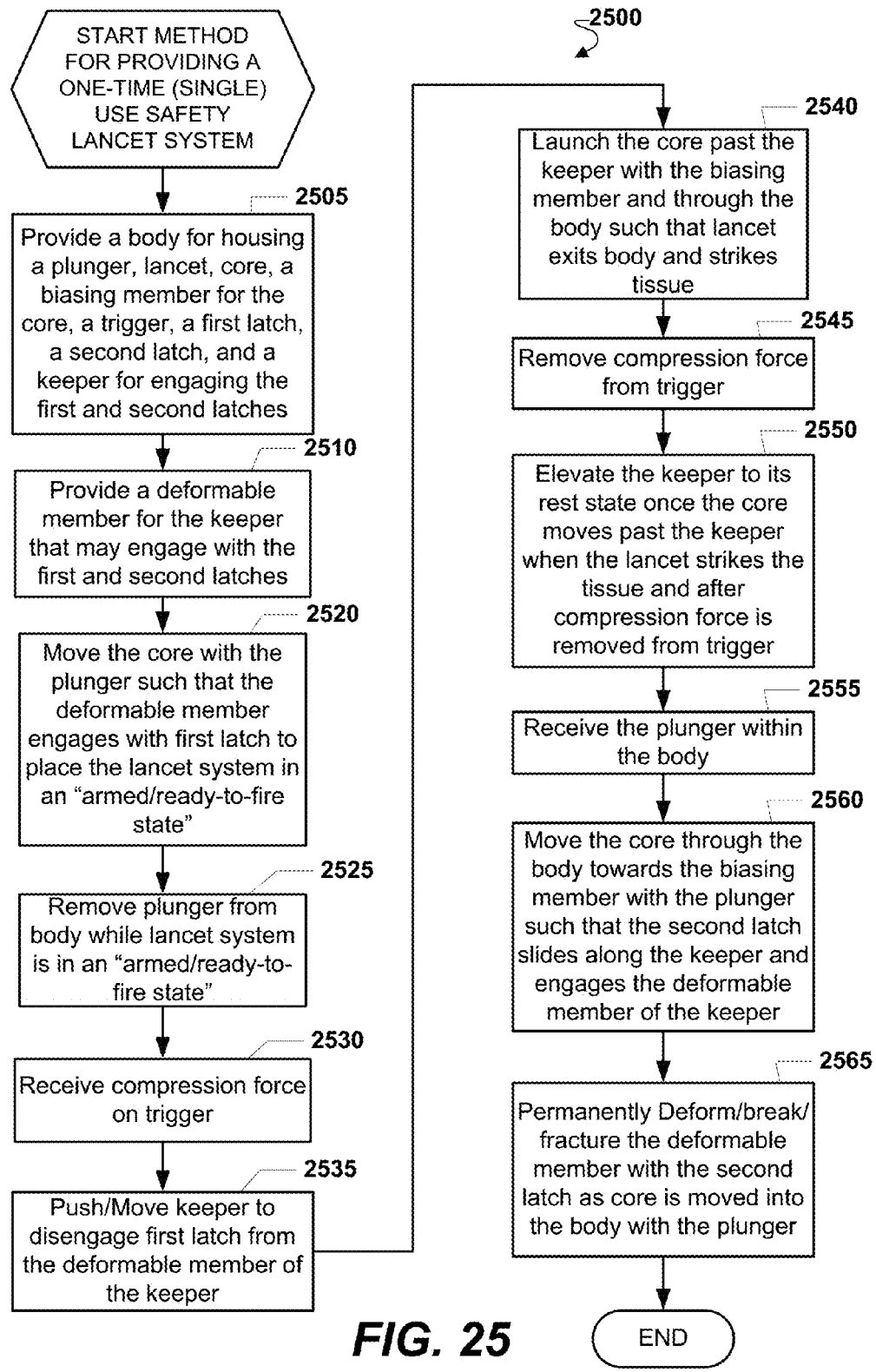
FIG. 25 is illustrates a logical flowchart for a method for providing a one-time (single) safety lancet system.

Referring now to FIG. 25, this figure illustrates a logical flowchart for a method 2500 for providing a one-time (single) use safety lancet system 101. Block 2505 is the first step of method 2500. In this block 2505, a body 20 may be provided for housing a plunger 10, a lancet 55, a movable core 30, a biasing member 50 for the core 30, a trigger 25, a first latch 35, a second latch 40, and a keeper 15 for engaging the first and second latches 35, 40. See FIGS. 2-3. As noted above, most of the materials and parts for the safety lancet system 101 may comprise plastic with some metal (i.e., the lancet 55 and biasing member 50). However, other materials, such as ceramics, rubber, etc. are within the scope of this disclosure.

Next, in block 2510 a deformable member 45 may be provided for the keeper 15. The deformable member 45 may be designed to engage and contact with the first latch 35 in the second latch 40 which are part of the movable core 30.

Next, in block 2520, the core 30 which is coupled to the plunger 10 may be moved such that the deformable member 45 engages with the first latch 35 to place the lancet system 101 in an "armed" or "ready-to-fire" state such as illustrated in FIG. 4 described above. As illustrated in FIG. 4, the deformable member 45 holds the first latch 35 any stationary state while the biasing member 50 has been compressed and also remains in a stationary/nonmoving state.

Subsequently, in block 2525, the plunger 10 which was used to engage the deformable member 45 with the first latch 35 of the core 30 is now removed from the lancet system 101. The plunger 10 typically covers and protects the lancet 55 prior to its single use in the system 101.

Next, in block 2530, a compression force may be received with the trigger 25 of the lancet system 101. FIG. 6 illustrates when a compression force is received with the trigger 25.

In block 2535, a keeper 15 is moved/pushed by the trigger 25 such that it disengages the first latch 35 from contacting the deformable member 45 of the keeper 15. Next, in block 2540, the core 30 is launched passed the keeper 15 with the biasing member 50 and through the volume defined by the body 20 such that the lancet exits the body 20 through an aperture 38 and strikes tissue 42. See FIGS. 9-10 which show the movement described in block 2540.

Next, in block 2545, the compression force may be removed from trigger 25. In block 2550, the keeper 15 may be elevated to its rest state once the core 30 this past the keeper 15 when the lancet 55 strikes tissue 42 and after the compression force is removed from the trigger 25. FIG. 11 illustrates when the core 30 has been pulled by the spring 50 away from the aperture 38 and towards the deformable member 45 such that the second latch 40 engages the deformable member 45. FIG. 11 as well as FIG. 12 illustrate this rest state of the keeper 15 after the lancet 55 has been fired into the tissue 42.

Subsequently, in block 2555, the plunger 10 may be received within the body 20 when a force is applied to one end of the plunger 10. In block 2560, the core 30 as it is being pushed by the plunger 10 through the body towards the biasing member 50 causes the second latch 40 slide along the keeper 15 and in which the deformable member 45 engages the second latch 40.

In block 2565, the deformable member 45 of the keeper 15 may be permanently performed/broken/fractured when the second latch of the core 30 is pushed against the deformable member 45 in response to a force applied to the plunger 10 such as illustrated in FIG. 14. As noted previously, FIG. 14 illustrates how a second latch 40 has already deformed/broken/fractured the deformable member 45. Specifically, in this exemplary embodiment, as illustrated in FIG. 14 the deformable member 45 was split into at least two pieces of debris. FIG. 15 illustrates a side view of the latest system 101 and at least one debris component from the previously solid deformable number 45. As explained above and as illustrated in FIG. 14, the lancet system 101 cannot be "armed" again because the first latch of the core 30 cannot engage any structure of the body 20 after the deformable member 45 is permanently deformed/broken/fractured.

Certain steps in the processes or process flows described in this specification naturally precede others for the invention to function as described. However, the invention is not limited to the order of the steps described if such order or sequence does not alter the functionality of the invention. That is, it is recognized that some steps may performed before, after, or parallel (substantially simultaneously with) other steps without departing from the scope and spirit of the invention. In some instances, certain steps may be omitted or not performed without departing from the invention. Further, words such as "thereafter", "then", "next", "subsequently" etc. are not intended to limit the order of the steps. These words are simply used to guide the reader through the description of the exemplary method.

Although a few embodiments have been described in detail above, those skilled in the art will readily appreciate that many modifications are possible in the embodiments without materially departing from this disclosure. Accordingly, such modifications are intended to be included within the scope of this disclosure as defined in the following claims.

For example, while the deformable member 45 has been described as being part of the keeper 15 which is part of the non-moving or stationary body 20, one of ordinary skill in the art recognizes that the deformable member 45 could be made part of the movable core 30. In such an embodiment, the "solid" keeper 15 may function to fracture deformable member 45 that is part of the movable core 30. Other alternate designs are possible and are within the scope of this disclosure.

In the claims, means-plus-function clauses are intended to cover the structures described herein as performing the recited function and not only structural equivalents, but also equivalent structures. Thus, as one simple mechanical example, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, sixth paragraph for any limitations of any of the claims herein, except for those in which the claim expressly uses the words 'means for' together with an associated function.

Although selected aspects have been illustrated and described in detail above, it will be understood that various substitutions and alterations may be made therein without departing from the scope of this disclosure, as defined by the following claims.

What is claimed is:

1. A one-time use lancet system comprising:
a body;
a spring coupled to the body;
a keeper having a deformable member; wherein the keeper is part of the body and
a core for supporting a lancet and having an end coupled to the spring, the core further comprising a first latch for engaging the deformable member when the lancet system is in an armed state; the deformable member being fractured after one use of the lancet system which prevents any subsequent arming of the lancet system.

2. The system of claim 1, wherein the core further comprises a second latch.

3. The system of claim 2, wherein the second latch permanently deforms or fractures the deformable member after arming of the lancet system.

4. The system of claim 1, wherein the spring comprises a coil spring.

5. The system of claim 1, wherein the keeper is biased such that it engages the first latch when the lancet system is armed.

6. The system of claim 5, wherein the keeper engages a trigger and the trigger enables launching of the core when a compressive force is applied to the trigger and when the lancet system is armed.

7. A method for providing a single-use lancet system, the method comprising:
providing a body for housing a plunger, a lancet, a core, a biasing member for the core, a trigger, a first latch, a second latch, and a keeper for engaging the first and second latches;
providing a deformable member for the keeper that may engage with the first and second latches;
moving the core with the plunger such that the deformable member engages with the first latch to place the lancet system in an armed state;
moving the keeper to disengage first latch from the deformable member of the keeper;
launching the core past the keeper with the biasing member and through the body such that lancet exits the body;
elevating the keeper to its rest state once the core moves past the keeper when the lancet strikes the tissue and after compression force is removed from trigger;
moving the core through the body towards the biasing member with the plunger such that the second latch slides along the keeper and engages the deformable member of the keeper; and
permanently fracturing the deformable member with the second latch as core is moved into the body.

8. The method of claim 7, further comprising: removing the plunger from body while lancet system is in the armed state.

9. The method of claim 7, further comprising: receiving a compression force on the trigger.

10. The method of claim 9, further comprising: removing the compression force from the trigger.

11. The method of claim 7, further comprising: receiving the plunger within the body.

12. The method of claim 7, wherein the lancet system cannot be armed again since first latch of core cannot engage any structure of the body after the deformable member is permanently fractured.

13. The method of claim 7, further comprising providing a lancet with a gage of between about 15 to about 35.

14. The method of claim 7, further comprising providing a lancet with a length that is measured from its exposure outside the core that is between about 1.2 millimeter to about 3.0 millimeters.

* * * * *